United States Patent [19]

Friese et al.

[11] Patent Number: 5,653,858
[45] Date of Patent: Aug. 5, 1997

[54] LIMIT CURRENT SENSOR FOR DETERMINING THE LAMBDA VALUE IN GAS MIXTURES

[75] Inventors: Karl-Hermann Friese, Leonberg; Werner Gruenwald, Gerlingen, both of Germany

[73] Assignee: Robert Bosch GmbH, Stuttgart, Germany

[21] Appl. No.: 495,654

[22] PCT Filed: Nov. 24, 1994

[86] PCT No.: PCT/DE94/01388

§ 371 Date: Jul. 27, 1995

§ 102(e) Date: Jul. 27, 1995

[87] PCT Pub. No.: WO95/15491

PCT Pub. Date: Jun. 8, 1995

[30] Foreign Application Priority Data

Dec. 3, 1993 [DE] Germany .................. 43 41 278.5

[51] Int. Cl.⁶ .................................. G01N 27/41
[52] U.S. Cl. ..................... 204/425; 204/426; 204/429
[58] Field of Search .................... 204/421–429

[56] References Cited

U.S. PATENT DOCUMENTS

| | | | |
|---|---|---|---|
| 4,231,733 | 11/1980 | Hickman et al. | 204/426 |
| 4,574,627 | 3/1986 | Sakurai et al. | 204/426 |
| 4,670,128 | 6/1987 | Mase et al. | 204/425 |
| 4,769,124 | 9/1988 | Okada et al. | 204/425 |

FOREIGN PATENT DOCUMENTS 3908393  1/1991  Germany .

*Primary Examiner*—T. Tung
*Attorney, Agent, or Firm*—Spencer & Frank

[57] ABSTRACT

A limit current sensor for determining lambda values of a gas mixture includes a solid electrolyte layer comprised of a material which conducts oxygen ions; an anode provided on a surface of the solid electrolyte layer and having a surface opposite the solid electrolyte layer which is exposed to a gas which is one of the gas mixture being measured or a reference gas; a first pumping cell comprising the anode and a first cathode provided on a surface of the solid electrolyte layer opposite the anode; a second pumping cell comprising the anode and a second cathode provided on the surface of the solid electrolyte layer on which the first cathode is provided and spaced apart from the first cathode; a diffusion layer which is provided across the first cathode and the second cathode in contact therewith and along surfaces thereof opposite the solid electrolyte layer, and which is in communication with the gas mixture to be measured so that diffusion of the gas mixture to be measured through the diffusion layer occurs along a diffusion path which reaches the first cathode prior to reaching the second cathode; and means for activating one pumping cell at a time based on a predetermined threshold value of oxygen concentration so that the first cathode is activated at oxygen concentrations within a range near a stoichiometric gas mixture where $\lambda=1$ and so that the second cathode is activated at higher oxygen concentrations.

14 Claims, 4 Drawing Sheets

5,653,858

LIMIT CURRENT SENSOR FOR DETERMINING THE LAMBDA VALUE IN GAS MIXTURES

BACKGROUND OF THE INVENTION

1. Field of the Invention

The invention is based on a limit current sensor for determining the lambda value in gas mixtures of the generic type of the main claim.

2. Description of the Related Art

The German Offenlegungsschrift 39 08 393 discloses a limit current sensor in which, in order to reduce the response time, a second pumping cell is provided with which a constant concentration of oxygen in the diffusion channel can be obtained. The second pumping cell serves to achieve the steady state equilibrium condition of the diffusion current in the diffusion channel at an early point in time. Shortening the length of the diffusion channel would also bring about a rapid response time, but at the same time would increase the limit current too strongly. Because of the limited current loading capacity of the electrodes when the concentrations of oxygen are high in a lean gas mixture, a minimum length of the diffusion channel is necessary.

For the use of the limit current sensor in the lean range ($\lambda>1$), the stoichiometric range ($\lambda=1$) and up to the rich range ($\lambda<1$) of the fuel/air ratio, it is known, from EP-B1-190 750, to expose the anode of the pumping cell to a reference atmosphere. In the lean range these sensors operate like the known lean sensors. The oxygen molecules are reduced at the cathode so that the oxygen ions migrate from the cathode to the anode through the solid $ZrO_2$ electrolyte. At the anode the ions are in turn converted into oxygen molecules and released into the atmosphere. Under stoichiometric conditions, there is a chemical equilibrium at the cathode so that there is no pumping current present. In the rich range, the oxygen ions are also fed from the cathode to the anode as a result of the applied pumping voltage. At the anode, they are in turn converted into oxygen molecules. The stream of oxygen ions flows in the opposite direction from that of the lean range. For this purpose, it is necessary to reverse the polarity of the pumping voltage. This is realized in that the level of the electromotive force occuring under stoichiometric conditions is used as switching signal.

In limit current sensors, a limit current is generally measured with a constant voltage applied to the two electrodes of the limit current sensor. With an oxygen-containing measurement gas, the limit current is linearly dependent on the partial pressure of the oxygen for as long as the diffusion of the gas to the cathode determines the speed of the reaction which is underway. Such limit current sensors which are exposed in particular to the measurement gas are suitable for detecting the concentration of oxygen in lean measurement gases. Between the electrodes, the limit current goes into the lean range as soon as the oxygen molecules passing to the cathode through the diffusion layer are transported away rapidly in the form of ions. In the rich range, the limit current occurs when a diffusion barrier is placed in front of the anode and the diffusion of $H_2$ and CO to the anode determines the speed of the entire reaction.

When the pumping voltage grows slowly from the 0 volt value, there are ohmic conditions present between the electrodes so that, as the pumping voltage increases, the pumping current rises until the diffusion limit current brings about the limitation of the pumping current. If the cathode did not have a diffusion barrier or if it were exposed to the measurement gas with only a low diffusion resistance, in particular at high partial pressures a diffusion which limits the pumping current would not occur, as a result of which the current/voltage behavior of the sensor would continue to adhere to the ohmic conditions. As a result, the pumping voltage continues to rise so that finally, even at values greater than 1 volt, it does not move into the limit current range and thus it does not become possible to measure the $O_2$ content. Such high pumping voltages lead to the solid electrolyte and the electrode being destroyed. On the other hand, at low partial pressures, even a low diffusion resistance would be sufficient. However, in order to use the limit current sensor for detecting a wide range extending from lean to rich, a sufficient diffusion resistance must be ensured. A sufficient diffusion resistance which is determined by a corresponding diffusion path of the measurement gas has, in the vicinity of stoichiometric conditions, the disadvantage that there is hardly any difference in concentration any more and thus even small fluctuations of measurement gas falsify the sensor signal. Also, in this ease, even small voltages are sufficient to destroy the solid electrolyte.

SUMMARY OF THE INVENTION

The limit current sensor according to the invention has the advantage that the sensitivity of the limit current sensor is increased in the region around the stoichiometric ratio ($\lambda=1$).

With the measures disclosed in the subclaims, advantageous developments of the limit current sensor according to the invention are possible. It is particularly advantageous to realize the two pumping cells with different diffusion resistances. A simple way of realizing different diffusion resistances is achieved if the cathodes of the two pumping cells are arranged with different diffusion paths in the diffusion barrier. Good results can be achieved if the diffusion path of the pumping cell with the higher sensitivity corresponds to 0.1 to 0.7 times, preferably 0.3 times, the diffusion path of the pumping cell with the longer diffusion path. A cost effective design of the limit current sensor is possible by providing a common anode with a single connection line for the two pumping cells.

BRIEF DESCRIPTION OF THE DRAWINGS

Two exemplary embodiments of the invention are represented in the drawing and in the subsequent description.

DESCRIPTION OF THE PREFERRED EMBODIMENTS

Figure 1:
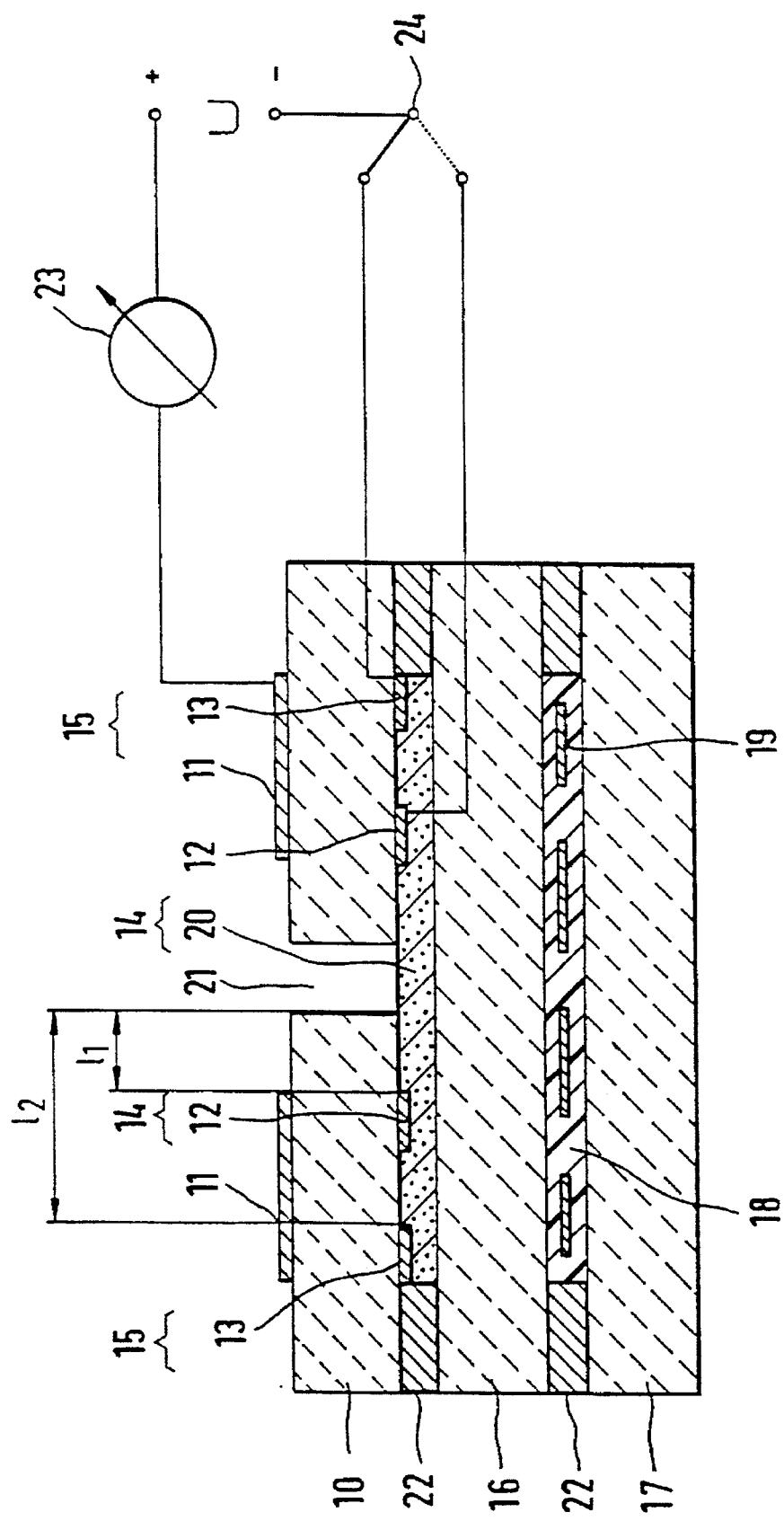
FIG. 1 shows a first exemplary embodiment of a limit current sensor according to the invention for lean exhaust gas.

The limit current sensor according to FIG. 1 has a first solid electrolyte film 10, consisting for example of yttrium-stabilized zirconium oxide, with an anode 11 and a first cathode 12 and a second cathode 13. The first cathode 12 forms with the anode 11 a first pumping cell 14 and the second cathode 13 forms with the anode 11 a second pumping cell 15. Arranged parallel to the first solid electrolyte film 10 are a second solid electrolyte film 16 and a third solid electrolyte film 17. A heater 19 which is embedded in an electrically insulating layer 18 is positioned between the two solid electrolyte films 16, 17. The insulating layer 18 consists for example of $Al_2O_3$. Instead of the solid electrolyte films 16 and 17, other ceramic films can also be used just as well, for example consisting of $Al_2O_3$. Of course, when electrically insulating ceramic films are used, the insulating layer 18 for embedding the heater 19 can be dispensed with.

In each case a gas-tight frame 22 which determines the distance and which also consists for example of zirconium oxide is provided between the first solid electrolyte film 10, the second solid electrolyte film 16 and the third solid electrolyte carrier 17.

Between the first solid electrolyte film 10 and the second solid electrolyte film 16 a diffusion channel 20 which forms a diffusion barrier for the measurement gas is realized, which diffusion channel 20 is connected to the measurement gas via a diffusion hole 21. The anode 11 and the two cathodes 12, 13 extend around the diffusion hole 21 for example in an annular shape. The first cathode 12 is positioned here with a diffusion path $1_1$ nearer to the diffusion hole 21 than the second cathode 13 with a diffusion path $1_2$. The diffusion path $1_1$ to the first cathode 12 is for example 0.3 times the diffusion path $1_2$ of the second cathode 13. In order to form an appropriate diffusion resistance, the diffusion channel 20 is filled with a porous material, consisting for example of $Al_2O_3$. Here, the size of the pores determines, inter alia, the diffusion resistance.

The anode 11 and the cathodes 12, 13 are connected to a pumping voltage source U, the connection to the cathodes 12, 13 being switchable as desired by means of a switch 24. In addition, an ammeter 23 is arranged in the circuit in order to measure the limit current $I_p$. For practical application in a motor vehicle, instead of the ammeter 23, a control unit is provided for controlling the fuel/air mixture.

Figure 2:
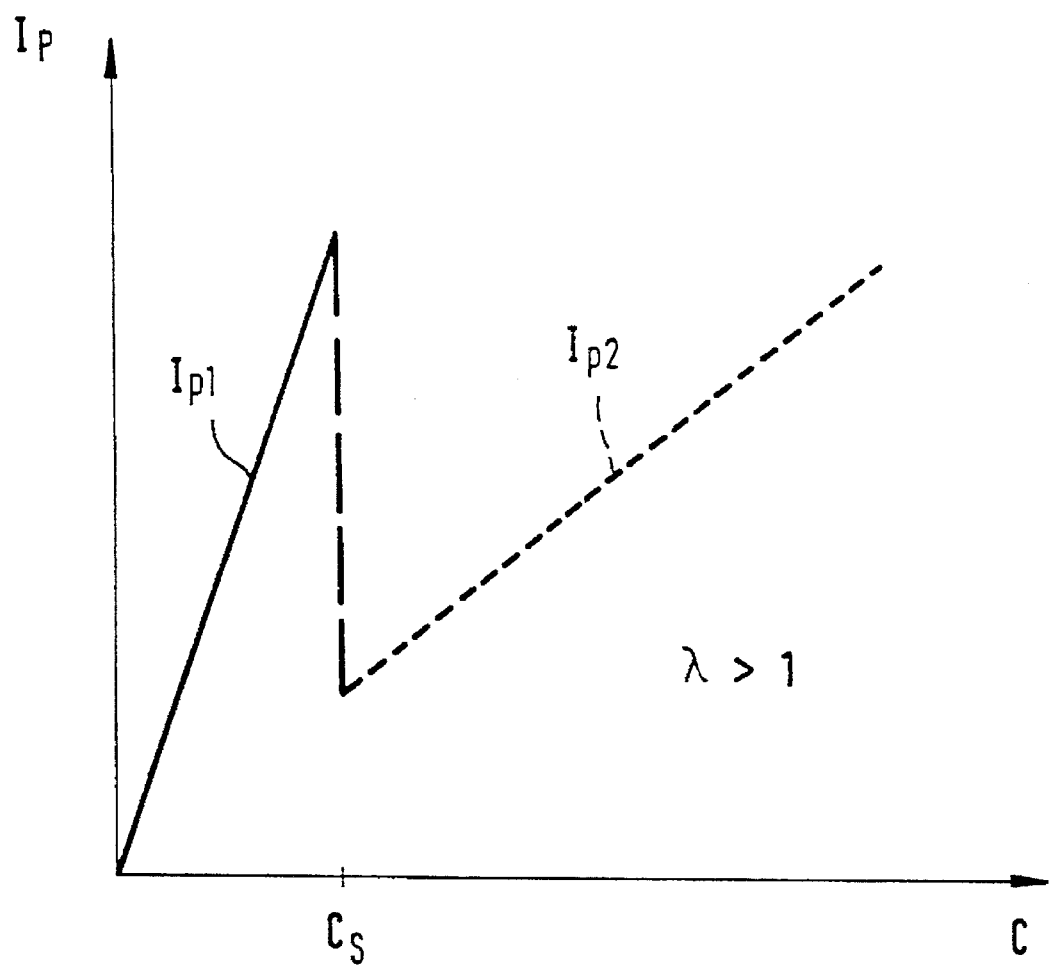
FIG. 2 shows the characteristic curve of the limit current plotted against the concentration of oxygen of the limit current sensor according to FIG. 1.

FIG. 2 shows the characteristic curve of the pumping current $I_p$ of the two pumping cells 14, 15 plotted against the $O_2$ concentration C. The limit current $I_p$ of the two pumping cells is measured by the ammeter 23. When there is a high concentration of oxygen in the measurement gas (air= 20.5%), the second cathode 13 is connected to the voltage source U via the switch 24. As the concentration C of oxygen decreases, the limit current $I_{p2}$ of the second pumping cell 15 is reduced. As soon as a predetermined threshold value $C_s$ of the concentration C of oxygen is reached, the pumping voltage U is applied to the first cathode 12. For this purpose, the switch 24 is activated in accordance with the dotted line in FIG. 1. The activation of the switch 24 is carried out by a control circuit (not illustrated), the threshold value $C_s$ being defined by means of a current-proportional pumping voltage. The limit current $I_{p1}$ which is now measured by the ammeter 23 is significantly higher with the same concentration of oxygen than the limit current $I_{p2}$ of the second pumping cell 15. As the concentration of oxygen decreases, the limit current $I_{p1}$ of the first pumping cell 14 becomes increasingly small until it becomes zero at a concentration of oxygen of $10^{-10}$ bar, which corresponds to a stoichiometric ratio ($\lambda=1$). The steepness of the characteristic curve of the limit current $I_{p1}$ of the first pumping cell 14 alone indicates that even small fluctuations in the $O_2$ concentration of the measurement gas in the vicinity of $\lambda=1$ bring about a significant change in the limit current $I_{p1}$. Finally, this signifies a higher sensitivity of the limit current sensor in the region near to $\lambda=1$. The size of the threshold value $C_s$ at which the switchover from the second pumping cell 15 to the first pumping cell 14 takes place is dependent on the positioning of the first cathode 12 in the diffusion channel 20.

Figure 3:
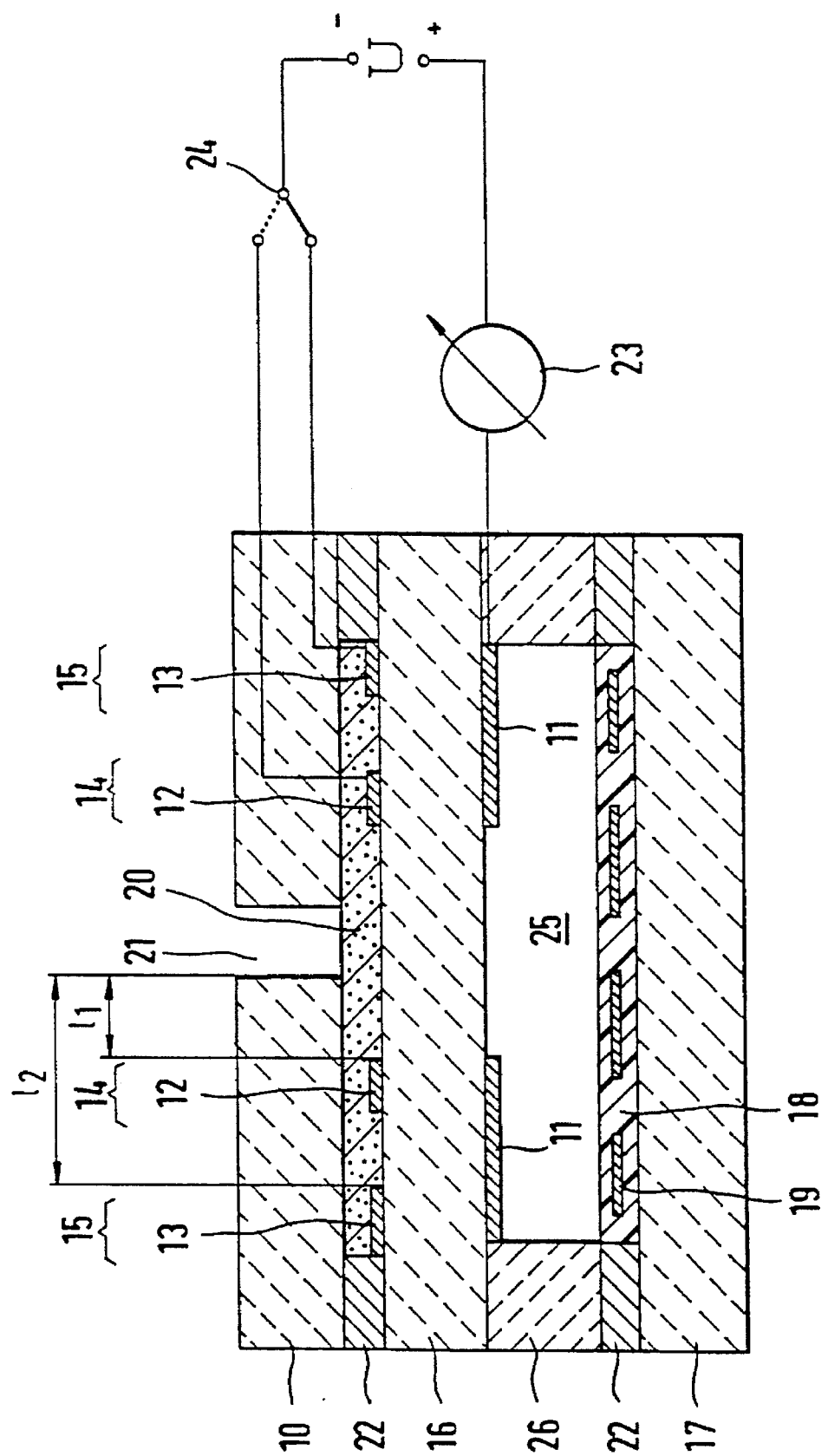
FIG. 3 shows a second exemplary embodiment of a limit current sensor for determining the lambda value of the exhaust gas ranging from lean exhaust gas to rich exhaust gas.

A second exemplary embodiment of a limit current probe which can be used as a broadband sensor from the lean range to the rich range of a gas mixture is shown in FIG. 3. In this limit current sensor, the anode 11 is arranged in a reference channel 25. The reference channel 25 is connected for example to the atmosphere. The measurement gas is fed, as in the case of the sensor according to FIG. 1, via the diffusion hole 21 and the diffusion barrier 20 to the two cathodes 12 and 13. The arrangement of the cathodes 12 and 13 and their diffusion path $1_1$ and $1_2$ corresponds to the embodiment according to FIG. 1. However, in the present exemplary embodiment, the cathodes 12, 13 are arranged on the second solid electrolyte film 16. The first solid electrolyte film 10 contains the diffusion hole 21, as in the first exemplary embodiment. The anode 11 is adjoined by a further ceramic film 26 in which the reference channel 25 is provided. In the present exemplary embodiment, the heater 19 with the insulating layer 18 is connected directly to the reference channel 25 for better heat conduction. However, it is equally conceivable to provide an additional ceramic film between the insulation layer 18 and the reference channel 25.

Figure 4:
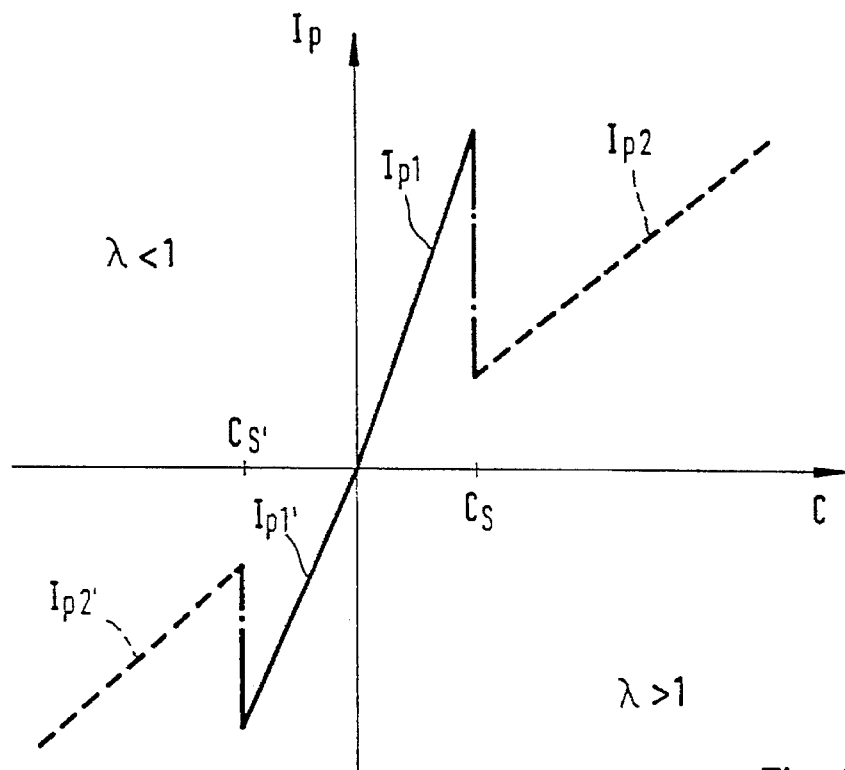
FIG. 4 shows a characteristic curve of the limit current plotted against the concentration of oxygen of the limit current sensor according to FIG. 3.
Figure 5:
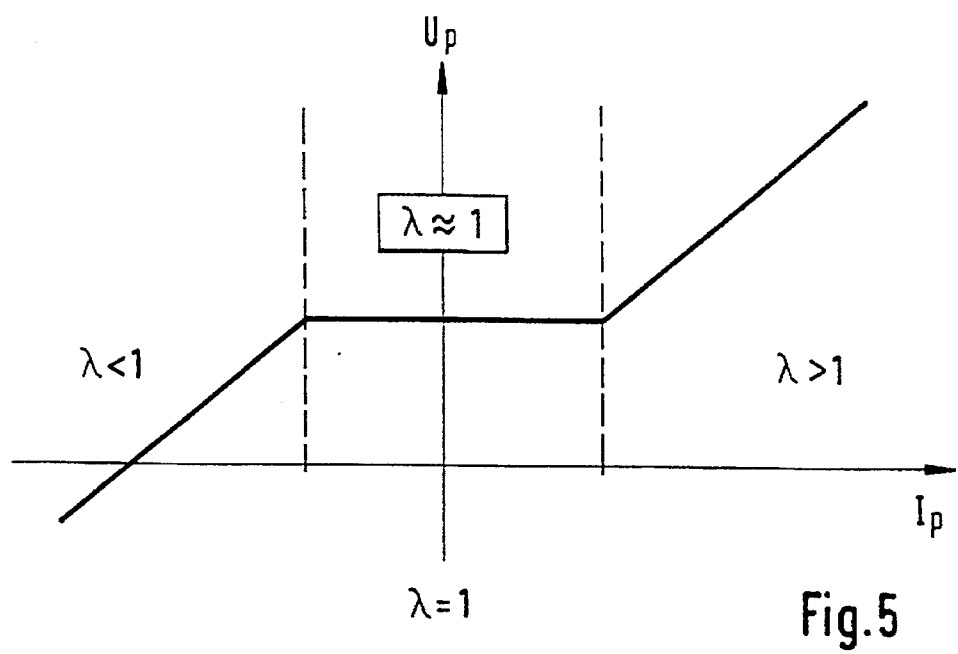
FIG. 5 shows the profile of the pumping voltage $U_p$ plotted against the pumping current $I_p$.

The characteristic curve illustrated in FIG. 4 shows the profile of the pumping current $I_p$ of a concentration of oxygen in the lean exhaust gas ($\lambda>1$) plotted against the concentration of oxygen ranging between $\lambda=1$ and a concentration of oxygen in the rich exhaust gas ($\lambda<1$). The concentration of oxygen in the rich exhaust gas indicates the incorrect amount of oxygen which is necessary to set the gas mixture to $\lambda=1$. In this context, the concentrations of oxygen are to be understood as those which have proven to have negative values in the coordinate system. The profile of the characteristic curve in the lean exhaust gas corresponds to the profile according to FIG. 2. Given further approximation to $\lambda=1$, the pumping voltage $U_p$ according to FIG. 5 is held at a constant value of for example 300 millivolts.

When $\lambda=1$, an electromotive force (Nernst voltage) which is opposed to the outer pumping voltage is obtained, as already described, as a result of which the limit current $I_{p1}$ which is measured by the ammeter 23 becomes zero. In this case, the partial pressure of the oxygen in the diffusion channel 20 becomes approximately $10^{-10}$ bar. At the transition into rich exhaust gas ($\lambda<1$), the electromotive force with approximately 900 millivolts predominates. However, this voltage is not effective since, on the one hand, it operates against the pumping voltage $U_p$ which is applied from outside and, on the other hand, it is reduced, principally at relatively large pumping currents, by the internal resistance of the voltage source of the electromotive force. If the pumping voltage $U_p$ applied from outside is not selected to be too large and the internal resistance of the voltage source of the electromotive force is small, an anodic limit current $I_{p1}$, develops under the influence of the electromotive force for $\lambda<1$, the second cathode 13 being in turn switched to by means of the switch 24 when a specific, adjustable threshold value $C_S$, is exceeded. Here, the limit current $I_{p1}$, measured by the meter 23, according to the dot-dash line drops suddenly to a lower value until the anodic limit current $I_{p2}$, is obtained at the second cathode 13. As the concentration of oxygen drops, the anodic limit current $I_{p2}$, continues to rise, but with a lower gradient than the anodic limit current $I_{p1}$, of the first pumping cell 14.

In order to switch over from the first cathode 12 to the second cathode 13, and vice versa, a threshold value for the limit current can also be set. When the corresponding pumping cell is operating, the system again operates with current-proportional pumping voltage.

The limit current sensor according to the invention is manufactured in a known way using lamination and screen printing technology and by means of subsequent co-sintering.

We claim:

1. A limit current sensor for determining lambda values of a gas mixture, comprising:

a solid electrolyte layer comprised of a material which conducts oxygen ions;

an anode provided on a surface of the solid electrolyte layer and having a surface opposite the solid electrolyte layer which is exposed to a gas which is one of the gas mixture being measured or a reference gas;

a first pumping cell comprising the anode and a first cathode provided on a surface of the solid electrolyte layer opposite the anode;

a second pumping cell comprising the anode and a second cathode provided on the surface of the solid electrolyte layer on which the first cathode is provided and spaced apart from the first cathode;

a diffusion layer which is provided across the first cathode and the second cathode in contact therewith and along surfaces thereof opposite the solid electrolyte layer, and which is in communication with the gas mixture to be measured so that diffusion of the gas mixture to be measured through the diffusion layer occurs along a diffusion path which reaches the first cathode prior to reaching the second cathode and so that the diffusion path to the second cathode has a length which is longer than the diffusion path to the first cathode whereby the second cathode has a higher resistance to diffusion than the first cathode; and control circuit means for activating one pumping cell at a time based on a predetermined threshold value of oxygen concentration so that the first cathode, which has a shorter diffusion path and a correspondingly lower diffusion resistance, is activated at oxygen concentrations within a range near a stoichiometric gas mixture where λ=1 and so that the second cathode, having a longer diffusion path and a correspondingly higher diffusion resistance, is activated at higher oxygen concentrations.

2. The limit current sensor as claimed in claim 1, wherein the surface of the anode opposite the solid electrolyte layer is exposed to the gas mixture being measured.

3. The limit current sensor as claimed in claim 1, wherein the surface of the anode opposite the solid electrolyte layer is exposed to a reference gas.

4. The limit current sensor as claimed in claim 1, wherein the predetermined threshold value for activating one pump cell is determined by measuring a pumping current.

5. The limit current sensor as claimed in claim 4, wherein activating one pumping cell is accomplished by switching over from one pumping cell to the other.

6. The limit current sensor as claimed in claim 1, wherein the predetermined threshold value for activating one pump cell is determined by measuring a current-proportional pumping voltage.

7. The limit current sensor as claimed in claim 6, wherein activating one pumping cell is accomplished by switching over from one pumping cell to the other.

8. The limit current sensor as claimed in claim 1, wherein the diffusion path for the first cathode has a diffusion path length ($l_1$), wherein the diffusion path for the second cathode has a diffusion path length ($l_2$), and wherein the diffusion path length ($l_1$) ranges between 0.1 and 0.7 times the diffusion path length ($l_2$) of the second cathode.

9. The limit current sensor as claimed in claim 8, wherein the diffusion path length ($l_1$) is 0.3 times the diffusion path length ($l_2$).

10. The limit current sensor as claimed in claim 1, wherein the anode of the first pumping cell and the anode of the second pumping cell are a common anode, and wherein the common anode is a common pumping electrode.

11. The limit current sensor as claimed in claim 1, wherein the first pumping cell has a pumping voltage which is maintained at a constant value.

12. The limit current sensor as claimed in claim 11, wherein the pumping voltage is smaller than the Nernst voltage.

13. The limit current sensor as claimed in claim 12, wherein the pumping voltage is 300 mV.

14. The limit current sensor as claimed in claim 1, wherein the gas mixture is exhaust gas from an internal combustion engine.

* * * * *